United States Patent [19]

Jones et al.

[11] 4,433,141

[45] Feb. 21, 1984

[54] INTERMEDIATE FOR USE IN THE PREPARATION OF CEPHALOSPORIN ANTIBIOTICS

[75] Inventors: William R. Jones, Greenford; Harish S. Trivedi, London; Timothy L. Gane, Ruislip, all of England

[73] Assignee: Glaxo Group Limited, London, England

[21] Appl. No.: 429,134

[22] Filed: Sep. 30, 1982

Related U.S. Application Data

[62] Division of Ser. No. 239,203, Mar. 3, 1981, Pat. No. 4,369,313, which is a Continuation of Ser. No. 152, 852, May 23, 1980, now abandoned.

[30] Foreign Application Priority Data

May 25, 1979 [GB] United Kingdom ................. 7918428

[51] Int. Cl.$^3$ ................. C07D 501/38; A61K 31/545
[52] U.S. Cl. ........................................ 544/25; 424/246
[58] Field of Search ...................... 544/24, 25; 424/246

[56] References Cited

U.S. PATENT DOCUMENTS

| | | | |
|---|---|---|---|
| 3,207,755 | 9/1965 | Abraham et al. | 544/24 |
| 3,234,224 | 2/1966 | Schenier et al. | 544/24 |
| 3,280,118 | 10/1966 | Eadley et al. | 544/24 |
| 3,422,099 | 1/1969 | Crast | 544/24 |
| 4,369,313 | 1/1983 | Jones et al. | 544/25 |

FOREIGN PATENT DOCUMENTS

| | | |
|---|---|---|
| 953695 | 3/1961 | United Kingdom . |
| 1028563 | 5/1965 | United Kingdom . |
| 1522140 | 8/1978 | United Kingdom . |

*Primary Examiner*—Nicholas S. Rizzo
*Attorney, Agent, or Firm*—Bacon and Thomas

[57] ABSTRACT

(6R,7R)-7-amino-3-(1-pyridiniummethyl)ceph-3-em-4-carboxylate dihydrochloride and its solvates are prepared in substantially pure form and can be acylated by conventional methods to yield a wide variety of cephalosporin antibiotics. The dihydrochloride is advantageously prepared in the form of its crystalline dihydrate. Processes for the preparation of the dihydrochloride and its solvates are described.

The dihydrochloride and its solvates are particularly useful in the preparation of (6R,7R)-7-[(Z)-2-(2-aminothiazol-4-yl)-2-(2-carboxyprep-2-oxyimino)acetamido]-3-(1-pyridiniummethyl)ceph-3-em-4-carboxylate, in the course of the preparation of which the novel N,N-dimethylformamide solvate of (6R,7R)-7-[(Z)-2-(2-tritylaminothiazol-4-yl)-2-(2-t-butoxyprop-2-oxyimino)acetamido]-3-(1-pyridiniummethyl)ceph-3-em-4-carboxylate may be isolated in substantially pure crystalline form.

1 Claim, No Drawings

INTERMEDIATE FOR USE IN THE PREPARATION OF CEPHALOSPORIN ANTIBIOTICS

This application is a division of application Ser. No. 239,203, filed Mar. 3, 1981, now U.S. Pat. No. 4,369,313, which is a continuation of application Ser. No. 152,852, filed May 23, 1980, now abandoned.

The present invention relates to new compounds which are valuable intermediates in the preparation of cephalosporin $C_A$ antibiotics.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. Cephalosporin antibiotics differ, for example, in the acylamido grouping at the 7β-position and/or the atom or group at the 3-position of the molecule. Among these cephalosporin antibiotics, various compounds wherein the 3-position is substituted by a 1-pyridiniummethyl group have been found to have particularly good antibacterial activity. One example of such a compound which has achieved outstanding commercial importance is the antibiotic having the approved name cephaloridine i.e. (6R,7R)-7-(2-thienylacetamido)-3-(1-pyridiniummethyl)ceph-3-em-4-carboxylate. We have recently prepared other cephalosporin compounds containing a 1-pyridiniummethyl group at the 3-position which have especially good antibacterial activity, particuarly against gram-negative organisms including those producing β-lactamases. These compounds contain a 7β-acylamido side chain of the formula:

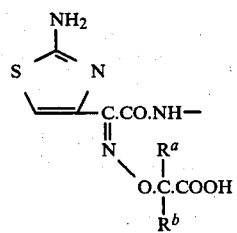

(I)

(wherein $R^a$ and $R^b$, which may be the same or different, each represent a $C_{1-4}$ alkyl group, or $R^a$ and $R^b$ together with the carbon atom to which they are attached form a $C_{3-7}$ cycloalkylidene group). Two compounds falling within this class and having outstanding antibiotic activity are (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate and (6R,7R)-7-[(Z)-2-(2-aminothiazol-4-yl)-2-(1-carboxycyclobut-1-oxyimino)acetamido]-3-(1-pyridiniummethyl)-ceph-3-em-4-carboxylate.

A method of preparing cephalosporin antibiotics having a 3-(1-pyridiniummethyl)group by acylation of the corresponding 7β-amino compound with an appropriate acylating agent is described in British Patent Specification No. 953,695. However, difficulties are encountered when using such a method in that it only leads to very low yields and the desired 7β-acylamido compound is only obtained with great difficulty, if at all, in a pure crystalline form. Furthermore, (6R,7R)-7-amino-3-(1-pyridiniummethyl)ceph-3-em-4-carboxylate itself is only obtained in low yields of poor quality material by existing methods and is thus not a satisfactory starting material for use in a commercial acylation process of the kind just referred to.

The above British Patent Specification refers to the preparation of cephalosporin compounds having a free amino group at the 7-position, including (6R,7R)-7-amino-3-(1-pyridiniummethyl)ceph-3-em-4-carboxylate, and reference is made to acid addition salts, including hydrochloride salts, formed at the 7-position primary amino group of such compounds, although there is no example illustrating the preparation of such salts. There is no mention in the above specification of the formation of di-acid addition salts of such compounds, and to the best of our knowledge and belief, only mono-acid addition salts of (6R,7R)-7-amino-3-(1-pyridiniummethyl)ceph-3-em-4-carboxylate have heretofore been referred to.

We have now discovered that the di(hydrogen chloride) acid addition salt of (6R,7R)-7-amino-3-(1-pyridiniummethyl)ceph-3-em-4-carboxylate can be acylated to produce a wide variety of cephalosporin compounds having a 1-pyridiniummethyl group in the 3-position and various acylamido groups in the 7-position. The use of the di(hydrogen chloride) salt results in surprisingly increased yields of cephalosporin compounds of high quality compared to processes involving the use of (6R,7R)-7-amino-3-(1-pyridiniummethyl)-ceph-3-em-4-carboxylate itself, or the mono(hydrogen chloride) salt of the compound.

Furthermore, we have discovered that the di(hydrogen chloride) acid addition salt of (6R,7R)-7-amino-3-(1-pyridiniummethyl)ceph-3-em-4-carboxylate can be prepared and isolated in a substantially pure form suitable for use as starting material in the acylation reactions described above.

According to one feature of the present invention therefore we provide as a new compound (6R,7R)-7-amino-3-(1-pyridiniummethyl)ceph-3-em-4-carboxylate dihydrochloride.

We further provide as new compounds the solvates, in particular the hydrates, of said dihydrochloride. An important solvate is the dihydrate since this may be obtained in a well-defined substantially pure crystalline form. For the sake of convenience, it should be understood that whenever reference is made herein to said dihydrochloride, this should also be taken to include the solvates if the context so admits.

The above-mentioned dihydrate is characterised by the following X-ray crystallographic data:

| d | I | d | I |
| --- | --- | --- | --- |
| 9.07 | m | 2.57 | m |
| 7.44 | w | 2.49 | 2vw |
| 6.57 | w | 2.44 | md |
| 6.17 | m | 2.37 | vw |
| 5.50 | vw | 2.33 | vw |
| 5.30 | w | 2.28 | vw |
| 4.94 | w | 2.22 | 2vw |
| 4.76 | w | 2.17 | vw |
| 4.44 | s | 2.12 | 2vw |
| 4.33 | s | 2.08 | vw |
| 3.90 | 2vw | 2.02 | vw |
| 3.82 | ms | 1.95 | 2vw |
| 3.75 | s | 1.92 | vw |
| 3.67 | ms | 1.87 | 2vw |
| 3.58 | w | 1.84 | 2vw |
| 3.39 | s | 1.81 | vw |
| 3.28 | w | 1.79 | vw |
| 3.18 | w | 1.76 | 2vw |
| 3.12 | vw | 1.70 | 2vw |

| d | I | d | I |
|---|---|---|---|
| 3.06 | 2vw | 1.67 | vw |
| 2.93 | s | 1.64 | 2vw |
| 2.89 | w | 1.62 | 2vw |
| 2.84 | m | 1.60 | 2vw |
| 2.75 | m | | |
| 2.67 | w | | |

'd' values in angstrom units
s = strong; m = medium; w = weak; v = very; 2v = vv; d = diffuse.

The samples were loaded into 0.3 mm diameter glass capillaries and photographed by the Debye Scherrer Method in 114.6 mm diameter cameras by exposure for 12 hours to CoK$_\alpha$ radiation and for 3 hours to CuK$_\alpha$ radiation.

The dihydrochloride salt has been found to be particularly applicable to the preparation of the cephalosporin antibiotics referred to above which contain in the 7-position an acylamido group of formula (I) above, particularly the two such compounds specifically named above.

The dihydrochloride may be prepared by any convenient method.

Thus, for example, the dihydrochloride may be prepared by a process comprising (A) N-deacylating a compound of formula

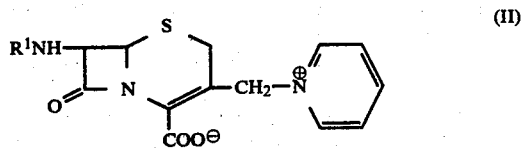

(II)

(wherein $R^1$ is an acyl group) or a corresponding compound having the group —COOR$^2$ at the 4- position wherein $R^2$ is a carboxyl protecting group and an associated anion $A^\ominus$, for example a halide ion, or a salt thereof by (i) contacting the appropriate compound with phosphorus pentachloride, converting the imide chloride to formed into an imino ether and hydrolyzing or alcoholysing the imino ether; or (ii) hydrolysing the appropriate compound in an aqueous medium in the presence of an enzyme catalyst and treating the 7β-amino compound so formed with hydrogen chloride (processes (A) (i) and (ii) being followed, where appropriate, by removal of the carboxyl protecting group $R^2$); or (B) reacting (6R,7R)-3-acetoxy methyl-7-aminoceph-3-em-4-carboxylic acid with pyridine and treating the 3-(1-pyridiniummethyl) compound so formed with hydrogen chloride.

The chemical method for deacylation of the 7-acylamino compound of formula (II) according to process (A) (i) above is described inter alia in British Patent Specification No. 1,241,655. The phosphorus pentachloride is preferably used in finely divided form.

It is generally necessary in such reactions to protect the 4-carboxyl group by a group ($R^2$) which may readily be split off as and when desired. This may conveniently be effected by silylation of the 4-carboxyl group.

It is generally convenient to react the 4-carboxyl group with a derivative of a silanol e.g. the corresponding chloride or amine. When preparing the esters on a commercial scale it may be advantageous to employ silyl chlorides for example, Me$_3$SiCl, in conjunction with a weak base such as, for example, N,N-dimethylaniline or N,N-diethylaniline. The silylating agent may also be a silazane, for example, hexamethyldisilazane, (Me$_3$Si)$_2$NH.

The reaction with phosphorus pentachloride may be carried out in an inert organic solvent such as a chlorinated hydrocarbon solvent, e.g. dichloromethane or chloroform. The reaction is generally carried out in the presence of a base, preferably an organic base. Suitable organic base, which preferably have a pKb of 4 to 6, include tertiary amines such as, for example, N,N-dimethylaniline or N,N-diethylaniline. If excess base is used in the preceding reaction it will not normally be necessary to use further base in this reaction.

Phosphorus pentachloride may be added to the solution of the cephalosphorin in molar excess and amounts of up to 10 molar excess may be used. It is uneconomical to use a large excess and we prefer to work with the cephalosporin compound and phosphorus pentachloride in molar proportions of from 1:2 to 1:3.

In effecting N-deacylations of silyl esters, advantageous results may be obtained by appropriate adjustment of the relative proportions of the reactants. Thus a large excess of base may produce unsatisfactory yields. A ratio of silyl ester:phosphorus pentachloride:base of 1:2:4 has been found to be useful. The 1:2:4 ratio of reactants is particularly effective when the base is N,N-dimethylaniline.

An advantage accruing from the use of silyl esters in the process according to the invention is that the esterifying group is removed under mild conditions and hence tends to be removed during one of the reaction stages e.g. during the formation of the imino ether.

The silyl ester group is thus easily split off by exposing the derivative to an excess of compound(s) containing active hydrogen, e.g., water, optionally with the addition of acids or bases, alcohols, polyhydric alcohols and phenols.

The temperature for the reaction of the phosphorus pentachloride with the cephalosporin may be from −60° to +25° C. Advantageously one operates within a temperature range of −50° C. to −10° C.

The imide chloride may be converted into the imino ether by reacting with a monohydric or polyhydric alcohol. The imino ether-forming compound may be a lower alkanol i.e. an alkanol having from 1 to 6 carbon atoms, for example methanol, ethanol, n-propanol, n-butanol, isopropanol or isobutanol, preferably methanol.

Advantageously, the imino ether-forming compound is a diol of the formula

where $R^A$ is a divalent alkylene or cycloalkylene group having up to 4 carbon atoms in the carbon chain linking the oxygen atoms. Such diols include ethylene glycol, propane-1,2- and -1,3-diol and the various butane diols, e.g. butane-1,3-diol.

The imino ether-forming compound may be used in substantial molar excess e.g. up to 75 over the cephalosporin compound. It may be used in solution in an inert organic solvent such as a chlorinated hydrocarbon e.g. dichloromethane.

Although the imino ether-forming compound may be added to the reaction solution we prefer to add the reaction solution to the imino ether-forming compound as this technique allows better control of the reaction system on a large scale.

The temperature for the reaction with the imino ether-forming compound may be from −40° to +30° C. The optimum temperature will depend, to some extent at least, on the reactants employed and in general we prefer to carry this step out at temperatures of from −20° to +20° C.

The reaction may be carried out in the presence of an organic base, the base required being usually carried through from the previous reaction.

On contacting the imino ether-forming compound and the previous reaction solution, the 7-amino compound is directly formed as the desired di(hydrogen chloride) salt. The dihydrate may be likewise directly isolated from appropriate media.

A wide variety of acyl groups containing for example 1-20 carbon atoms may be removed from 7β-acylamido cephalosporin compounds by the above process. Such acyl groups include those having the general formula $R^B CH_2 CO-$ where $R^B$ is aryl (carbocyclic or heterocyclic), cycloalkyl, substituted aryl, substituted cycloalkyl, or a non-aromatic heterocyclic group. Examples of this group include phenylacetyl, substituted phenylacetyl, thienyl-2- and -3-acetyl. Other acyl groups which may be used include 5-amino-adipoyl or 5-aminoadipoyl having one or both of the carboxyl and amino groups thereof blocked.

The above described 7β-acylamino compound of formula (II) may also be deprotected using enzymatic methods, i.e. enzymatic hydrolysis of the 7β-acylamido compound, e.g. using amidohydrolase enzyme preparations to effect hydrolysis of (6R,7R)-7-(2-thienylacetamido)-3-(1-pyridiniummethyl)ceph-3-em-4-carboxylate or its phenylacetamido analogue.

The enzyme may be added directly as an aqueous solution to the reaction solution to be catalysed. It may also be added in solid form obtained, for example, by freeze drying. The enzyme may be used in an immobilized form in or on a suitable matrix. This can take a variety of forms which include, for example, the occlusion of the enzyme in a matrix, for example, a glass or an artificial polymer e.g. cellulose triacetate, in fibrous form, or insolubilisation on a membrane. Such immobilized forms are described, for example in British Pat. No. 1,224,947 and in Belgian Patent No. 782,646.

Preferred enzymes for use in the above-mentioned hydrolysis reaction include amidohydrolase preparations derived from *E. coli* and Comamonas organisms as appropriate.

The immobilized enzyme may be added to a solution of the protected 7β-amino substrate and the reaction allowed to proceed desirably at from 20° to 70° C., e.g. about 37° C. and at constant pH e.g. from 6.5 to 8.0 for example about 7.0. The pH may be held constant by automatic addition of base to the reaction mixture. Up to 4 hours is generally sufficient for optimum hydrolysis to occur in one cycle and the reaction mixture may then be filtered in order to remove the immobilized enzyme. The dihydrochloride may be isolated by addition of the filtrate to a cation exchange resin and subsequent elution with, for example, pyridine/water, followed by concentration of the eluate and treatment of the residue with hydrochloric acid.

When preparing the dihydrochloride by enzymatic deacylation of the 7β-acylamido compound it may be advantageous to isolate the 7β-amino compound in the form of its monoperchlorate salt, and subsequently form the dihydrochloride. The monoperchlorate of (6R,7R)-7-amino-1-(1-pyrindiummethyl)ceph-3-em-4-carboxylate, which is a new compound, can be isolated in a substantially pure crystalline form.

The dihydrochloride salt according to the present invention may also be prepared by nucleophilic displacement of (6R,7R)-3-acetoxymethyl-7-aminoceph-3-em-4-carboxylic acid with pyridine and recovery of the resulting 3-(1-pyridiniummethyl) compound as the dihydrochloride. The nucleophilic displacement reaction may be effected in conventional manner, e.g. as described in British Patent Specification No. 1,028,563. As described in the latter specification, a convenient procedure for the nucleophilic displacement is to react the 3-acetoxymethyl compound in water with an excess of the pyridine nucleophile, followed by recovery of the desired compound by treatment with hydrochloric acid.

The dihydrochloride may conveniently be prepared as the dihydrate. This may be effected by contacting the reaction mixture with water or an aqueous medium or, if necessary, an aqueous solution of hydrogen chloride, or by dissolving the dihydrochloride, possibly in a semi-purified state, in aqueous hydrochloric acid and thereafter precipitating the dihydrochloride dihydrate therefrom by addition of a suitable reagent e.g. a lower alkanol.

As mentioned earlier, (6R,7R)-7-amino-3-(1-pyridiniummethyl)ceph-3-em-4-carboxylate dihydrochloride is of use in the preparation of a wide variety of 7β-acylamido cephalosporin compounds of formula

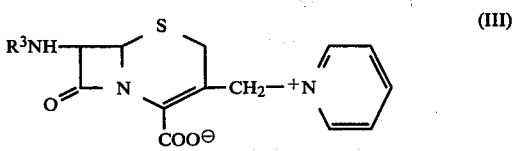

wherein $R^3$ is an acyl group different from the group $R^1$ in formula (II) above), by for example reaction of the dihydrochloride with an acid of formula $R^3 OH$ 

(wherein $R^3$ is an acyl group in which any reactive group may be protected) or an acylating agent corresponding thereto, followed, where necessary, by removal of any protecting groups.

Thus, the present invention provides a process for the preparation of a compound of formula (III) as defined above, which comprises forming (6R,7R)-7-amino-3-(1-pyridiniummethyl)-ceph-3-em-4-carboxylate dihydrochloride by deacylation of a compound of formula (II) by process (A) (i) or (ii) as hereinbefore described and acylating the said compound with an acid of formula $R^3 OH$ 

(wherein $R^3$ is as defined above) or an acylating agent corresponding thereto, followed, where necessary, by removal of any protecting groups.

$R^3$ may be any one of a large number of acyl groups containing 1-20 carbon atoms; such groups include those having the general formula $R^B CH_2 CO-$ wherein $R^B$ is as defined above, in particular a 5 or 6 membered heterocyclic aryl group containing 1-4 heteroatoms selected from O, N and S, for example thienyl, furyl or 2-aminothiazolyl.

The acyl group may contain an imino group, for example an oxyimino group of the formula

wherein $R^C$ may for example be a $C_{1-4}$ alkyl group or a $C_{3-7}$ cycloalkyl group, optionally substituted by a carboxyl group.

A particularly important use for the dihydrochloride according to the present invention is in the preparation of 3-(1-pyridiniummethyl)cephalosporins containing a 7β-acylamido side chain of formula (I) above. These compounds may be prepared by reacting the above dihydrochloride with an acid of formula

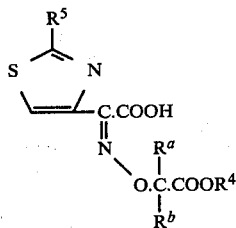

(IV)

(wherein $R^a$ and $R^b$ are as hereinbefore defined; $R^4$ represents a carboxyl protecting group, e.g. the residue of an ester-forming aliphatic or araliphatic alcohol containing 1-20 carbon atoms and $R^5$ is an amino or protected amino group) or with an acylating agent corresponding thereto followed, where necessary, by the removal of protecting groups.

Acylating agents which may be employed in the last mentioned process include acid halides, particularly acid chlorides or bromides. Such acylating agents may be prepared by reacting an acid (IV) or a salt thereof with a halogenating agent, e.g. phosphorus pentachloride, thionyl chloride or oxalyl chloride.

Acylations employing acid halides may be effected in aqueous and non-aqueous reaction media, conveniently at temperatures of from −50° to +50° C., preferably −20° to +30° C., if desired in the presence of an acid binding agent. Suitable reaction media include aqueous ketones such as aqueous acetone, esters such as ethyl acetate, halogenated hydrocarbons such as dichloromethane, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (IV) may themselves be used as acylating agents in the above-described acylation process. Acylations employing acids (IV) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids of formula (IV) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorous acids), sulphuric acid or aliphatic or aromatic sulphonic acids (for example toluene-p-sulphonic acid). An activated ester may conveniently be formed in situ using, for example, 1-hydroxybenzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. dichloromethane, tetrahydrofuran, dimethylformamide or acetonitrile.

If desired, the above acylation reactions may be carried out in the presence of a catalyst such as 4-dimethylaminopyridine.

The acids of formula (IV) and acylating agents corresponding thereto may, if desired, be prepared and employed in the form of their acid addition salts.

During the above acylation reaction, it may be necessary to protect the $NH_2$ group of the aminothiazolyl moiety, for example by tritylation, acylation (e.g. chloroacetylation), protonation or other conventional) methods. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water or, in the case of a chloroacetyl group, by treatment with thiourea.

Carboxyl protecting groups used in the compounds of formula (III) are desirably groups which may readily be split off as desired.

Suitable carboxyl protecting groups are well known in the art, a list of representative protected carboxyl groups being included in British Pat. No. 1,399,086. Preferred protected carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. Carboxyl protecting group(s) may subsequently be removed by any of the appropriate methods disclosed in the literature; thus, for example, acid or base catalysed hydrolysis is applicable in many cases, as are enzymatically-catalysed hydrolyses.

A particularly preferred embodiment of the above-described acylation process involves the use of an acid of formula (IV) (wherein $R^a$ and $R^b$ are both methyl groups, $R^4$ is for example a t-butyl group and $R^5$ is a protected amino group, e.g. a tritylamino group) or an acylating agent corresponding thereto, preferably the acid chloride. The resulting product, i.e. (6R,7R)-7-[(Z)-2-(2-tritylaminothiazol-4-yl)-2-(2-t-butoxycarbonylprop-2-oxyimino)acetamido]-3-(1-pyridiniummethyl)ceph-3-em-4-carboxylate may be isolated from a N,N-dimethylformamide medium as a N,N-dimethylformamide solvate in a crystalline form and of a high degree of purity. The N,N-dimethylformamide solvate is a new compound, and is a useful intermediate in the preparation of (6R,7R)-7-[(Z)-2-(2-aminothiazol-4-yl)-

2-(2-carboxyprop-2-oxyimino)acetamido]ceph-3-em-4-carboxylic acid as described in copending application No. [CE 254]. The amino and carboxyl protecting groups may thereafter be removed e.g. by treatment with a mixture of hydrochloric acid and formic acid to yield the corresponding deprotected compound in the form of its dihydrochloride in high yield and high purity.

In order that the invention may be well understood the following examples are given by way of illustration only. In the examples cephaloridine is (6R,7R)-7-(2-thienylacetamido)-3-(1-pyridiniummethyl)ceph-3-em-4-carboxylate; $PCl_5$ is phosphorus pentachloride; HPLC is high pressure liquid chromatography and NMR is nuclear magnetic resonance spectroscopy. The term "International Unit" used herein indicates the quantity of enzyme which will hydrolyze 1 micromole of penicillin G per minute at 37° C. Zerolit is a strongly acidic cationic exchange resin with polystyrenedivinylbenzene cross-linking.

EXAMPLE 1

(a)

(6R,7R)-7-Amino-3(1-pyridiniummethyl)ceph-3-em-4-carboxylate dihydrochloride

A stirred suspension of cephaloridine (4.15 g) in dichloromethane (30 ml) was treated with N,N-dimethylaniline (5.09 ml) and chlorotrimethylsilane (2.52 ml). This mixture was stirred at 30°–35° for one hour and then cooled to $-28°$ and treated with $PCl_5$ (4.16 g), stirred at $-25°$ to $-30°$ for another hour and then poured into a stirred cooled ($-20°$) solution of butane-1,3-diol (8.1 ml) and dichloromethane (20 ml). The solution was allowed to attain 0° over 30 minutes, and the precipitated solid (A) was filtered, washed with dichloromethane and dried in vacuo. It was redissolved in methanol (17.5 ml), stirred and diluted with dichloromethane (87.5 ml). The precipitated solid was filtered off, washed with dichloromethane and dried in vacuo to yield the *title compound* as a white solid (3.2 g), λmax (pH 6 buffer) 258 nm ($E_1 \, _{cm}^{1\%}$ 318) ($\epsilon$, 11,583); $\tau(D_2O)$ 0.95, 1.32 and 1.84 (pyridinium protons), 4.10 to 4.46 (AB quartet, J=16 Hz, 2H, =C$^1$—CH$_2$), 4.56 (d, J=5 Hz 1H, (C$_7$—H), 4.70 (d, J=5 Hz, 1H, C$_6$—H), 6.14 to 6.50 (AB quartet, J=17 Hz, 2H, C$_2$—H).

(b) Solid (A) prepared as in Example 1(a) above (8 g) was dissolved in N hydrochloric acid (25 ml). Addition of isopropanol (95 ml) precipitated the crystalline *title compound* as a dihydrate (4.95 g). $\tau(D_2O)$ 1.02; 1.36 and 1.87 (pyridinium protons); 4.2+4.55 (AB quartet, J=14 Hz, —CH$_2$—); 4.62 (d, J=5 Hz, C$_7$—H); 4.74 (d, J=5 Hz, C$_6$—H); 6.19+6.38 (AB quartet, J=18 Hz, C$_2$—H). Water content by Karl Fischer method, 9.4%.

Found C, 39.33; H, 4.78; N, 10.68; S, 8.1; Cl, 17.4% $C_{13}H_{15}N_3O_3SCl_2.2H_2O$ requires C, 39.0; H, 4.78; N, 10.5; S, 8.01; Cl, 17.72%.

(c) A solution of cephaloridine (2.0 g, 4.81 m mole) in water (50 ml) was treated with immobilised *E.coli* amidohydrolase enzyme (activity of 1.5 International Units per mg; 2.5 g). The reaction mixture was stirred for 1 hour at 30° and a pH of 7 was maintained during this period by titration with M ammonium hydroxide. The reaction mixture was then filtered. The filtered reaction mixture was passed down a column of Zerolit 225 H+ (50 ml, 100–200 mesh, 8% cross linking) and eluted with distilled water to pH 6. The product was eluted from the column with 10% pyridine in water, and the eluate concentrated under reduced pressure. The residue was dissolved in methanol (20 ml), concentrated hydrochloride acid (0.962 ml, 9.62 m mole) added, and the solution diluted with ethanol and dichloromethane to give the *title compound* in 2 crops (1.25 g) $\tau(D_2O)$ identical to that in Example 1(a), λmax (pH 6 buffer) 258($E_1 \, _{cm}^{1\%}$ 315, $\epsilon$11,480) and $\lambda_{infl}$ at 273($E_1 \, _{cm}^{1\%}$ 194, $\epsilon$7,070), impurities by HPLC 0.3%, chlorine; found: 19.9, calculated for $C_{13}H_{15}N_3Cl_2O_3S$ 19.5%.

EXAMPLE 2

(a)

(6R,7R)-7-[(Z)-2-(2-Tritylaminothiazol-4-yl)-2-(2-t-butoxycarbonylprop-2-oxyimino)acetamido]-3-(1-pyridiniummethyl)ceph-3-em-4-carboxylate (Z)-2-(2-t-Butoxycarbonylprop-2-oxyimino)-2-(2-tritylaminothiazol-4-yl) acetic acid (3.44 g) was added to a stirred solution of $PCl_5$ (1.38 g) in dichloromethane (60 ml), cooled to $-10°$. The resulting solution was stirred at $-5°$ for 30 minutes, and then cooled to $-10°$. Triethylamine (1.33 g) was added, followed by water (20 ml). The mixture was stirred for 3 minutes at 0°, when the lower phase was added over 10 minutes to a stirred suspension of (6R,7R)-7-amino-3-(1-pyridiniummethyl)ceph-3-em-4-carboxylate dihydrochloride (2.19 g; prepared according to Example 1(a)) in a mixture of N,N-dimethylacetamide (30 ml)/acetonitrile (30 ml) containing triethylamine (3.03 g), cooled to $-10°$. The mixture was stirred for 45 minutes at $-10°$ to $-5°$, followed by 1 hour without cooling. Methanol (1 ml) was added. Dichloromethane was removed by evaporation under reduced pressure. The residual solution was added to water (300 ml) with stirring to precipitate the *title compound* (4.89 g; containing approximately 1 mole of N,N-dimethylacetamide). $\tau(CDCl_3)$; 2.78 (s, —(C$_6$H$_5$)$_3$); 3.37 (s, -thiazole); 0.35, 1.80, 2.12 (pyridinium); 4.18 (m, —C$_7$); 4.95 (—C$_6$); 8.66 (s, -t-butyl); 8.50 (s, —(CH$_3$)$_2$).

(b)

(6R,7R)-7-[(Z)-2-(2-Aminothiazol-4-yl)-2-(2-carboxyprop-2-oxyimino)acetamido]-3-(1-pyridiniummethyl)-ceph-3-em-4-carboxylate dihydrochloride The product from Example 2(a) (3.38 g) was dissolved in 98% formic acid (20 ml) with stirring. Concentrated hydrochloric acid (1.2 ml) was added, and the mixture was stirred for 1 hour. The precipitated solid was removed by vacuum filtration. Solvent was removed from the filtrate by evaporation under reduced pressure to leave an oil which was triturated with acetone (30 ml) to give the *title compound* (2.20 g). $\tau(D_2O/$NaHCO$_3$); 3.08 (s, —thiazole); 1.06, 1.44, 1.93 (pyridinium); 4.16 (d, J5 Hz, —C$_7$); 4.74 (d, J5 Hz, —C$_6$); 8.55 (s, —CH$_3$)$_2$). Acetone by NMR, 1 mole. Water content, 5% (Karl Fischer method). Chlorine, found 10.1% ($C_{22}H_{24}N_6O_7S_2Cl_2$+acetone (1 mole)+water (5%) requires Cl, 10.0%.

EXAMPLE 3

(a) (6R,7R)-7-[(Z)-2-(2-Tritylaminothiazol-4-yl)-2-(2-t-butoxycarbonylprop-2-oxyimino)acetamido]-3-(1-pyridiniummethyl)ceph-3-em-4-carboxylate (6R,7R)-7-amino-3-(1-pyridiniummethyl)ceph-3-em-4-carboxylate dihydrochloride dihydrate (2.18 g), from Example 1(b) above was reacted as in Example 2(a) above to give the *title compound* (4.03 g). $\tau(DMSO-d_6)$; 2.4–3.0 (m, —(C$_6$H$_5$)$_3$); 3.33 (s, -thiazole); 0.49, 1.40 1.84

(pyridinium); 4.39 (m, —C$_7$); 4.94 (d, J5 Hz, —C$_6$); 8.65 (s, -t-butyl); 8.62 (s, —(CH$_3$)$_2$).

(b)

(6R,7R)-7-[(Z)-2-(2-Aminothiazol-4-yl)-2-(2-carboxy-prop-2-oxyimino)acetamido]-3-(1-pyridiniummethyl)-ceph-3-em-4-carboxylate dihydrochloride

The product from Example 3(a) (3.8 g) was treated as in Example 2(b) to give the *title compound* (2.17 g). τ(D$_2$O/NaHCO$_3$); 3.08 (s, -thiazole); 1.06, 1.42, 1.94 (pyridinium); 4.17 (d, J5 Hz, —C$_7$); 4.74 (d, J5 Hz, —C$_6$); 8.54 (s, —(CH$_3$)$_2$).

EXAMPLE 4

(a)

(6R,7R)-7-[(Z)-2-(2-Tritylaminothiazol-4-yl)-2-(1-t-butoxycarbonylcyclobut-1-oxyimino)acetamido]-3-(1-pyridiniummethyl)ceph-3-em-4-carboxylate

PCl$_5$ (1.38 g) was dissolved in 60 ml of dichloromethane. The solution was cooled to −10° and (Z)-2-(1-t-butoxycarbonylcyclobut-1-oxyimino)-2-(2-tritylaminothiazol-4-yl) acetic acid (3.48 g) was added. The solution was stirred at −5° for 30 minutes. Triethylamine (1.8 ml) was added, followed by water (20 ml). The mixture was stirred at 0° C. for 3 minutes. The lower phase was then added to a pre-cooled mixture of (6R,7R)-7-amino-3-(1-pyridiniummethyl)-ceph-3-em-4-carboxylate dihydrochloride (2.18 g prepared as described in Example 1(a) in dimethylacetamide (30 ml) and acetonitrile (30 ml, with triethylamine (4.2 ml) added at −10° C.

The reaction mixture was stirred for 45 minutes between −5° C. and −10° C. Cooling was then removed and the reaction was stirred for a further hour, ambient temperature being attained during this time. The solvent was removed under reduced pressure and the residue partitioned between ethyl acetate and water. The organic phase was washed with brine and the combined aqueous extracts extracted with ethyl acetate. The combined ethyl acetate extracts were dried in the presence of charcoal and the solvent was removed under reduced pressure. The residue was triturated with isopropyl ether to give the *title compound* (3.80 g) νmax (Nujol) 1780 cm$^{-1}$ (β-lactam) τ(CDCl$_3$) includes 2.74 (s, trityl) 8.66 (s, t-butyl).

(b)

(6R,7R)-7-[(Z)-2-(2-Aminothiazol-4-yl)-2-(1-carboxycyclobut-1-oxyimino)acetamido]-3-(1-pyridiniummethyl)ceph-3-em-4-carboxylate dihydrochloride

(6R,7R)-7-[(Z)-2-(2-tritylaminothiazol-4-yl)-2-(1-t-butoxycarbonylcyclobut-1-oxyimino)acetamido]-3-(1-pyridiniummethyl)ceph-3-em-4-carboxylate, (2.57 g from Example 4(a)) was stirred at ambient temperature in a mixture of 98% formic acid (15 ml), and concentrated hydrochloric acid (0.9 ml) for one hour. The mixture was then filtered and the solvent removed under reduced pressure. The resulting residue was triturated with acetone to produce the *title compound* (1.79 g). νmax (Nujol) 1785 cm$^{-1}$ (β-lactam) τvalues (D$_2$O+NaHCO$_3$) include 1.05, 1.42, 1.91 (m, pyridinium protons), 3.01 (s, aminothiazole proton) 4.13 (d, J=5 Hz, C$_7$ proton), 4.68 (d, J=5 Hz, C-6 proton) 7.4–8.4 (broad m, cyclobutyl protons) dimethylacetamide (⅓ mole) and acetone (⅛ mole) by NMR. Water content 7.4% (Karl Fischer method). Chlorine, found 9.2% (C$_{23}$H$_{24}$N$_6$O$_7$S$_2$Cl$_2$+⅓ mole dimethylacetamide +½ mole acetone +7.4% water requires Cl, 9.5%).

EXAMPLE 5

(6R,7R)-7-Amino-3-(1-pyridiniummethyl)ceph-3-em-4-carboxylate dihydrochloride dihydrate

A stirred suspension of cephaloridine (4.15 g) in dichloromethane (30 ml) was treated with N,N-dimethylaniline (5.09 ml) and chlorotrimethylsilane (2.52 ml). This was stirred at room temperature for one hour and then cooled to −30° and treated with PCl$_5$ (4.16 g), stirred at −25° to −30° for another hour and then poured into a precooled (−30°) solution of butan-1,3-diol, (8.1 ml) in dichloromethane (20 ml). The temperature of the resultant mixture was adjusted to −20° and allowed to attain 0° over 30 minutes. To this resultant suspension was added water (20 ml). The mixture was stirred and the aqueous layer separated. The organic layer was re-extracted with more water (5 ml). The combined aqueous extracts were diluted with isopropyl alcohol (100 ml) and the crystalline solid was filtered, washed with some isopropyl alcohol and dried in vacuo for several hours and then allowed to equilibrate at room temperature for several hours to yield the *title compound* as a crystalline solid (3.17 g) λmax (pH 6 buffer) 318 nm (E$_{1\,cm}$1%, 318); Elemental analysis found, Cl: 17.4, H$_2$O:9.5 (Karl Fischer method) C$_{13}$H$_{19}$N$_2$O$_5$Cl$_2$S requires Cl, 17.7; H$_2$O.9.3.

EXAMPLE 6

(a)

(6R,7R)-7-[(Z)-2-(2-Tritylaminothiazol-4-yl)-2-(2-t-butoxycarbonylprop-2-oxyimino)acetamido]-3-(1-pyridiniummethyl)ceph-3-em-4-carboxylate, N,N-dimethylformamide solvate

Finely powdered product of Example 2(a) (4 g) was added to stirred N,N-dimethylformamide (15 ml) at 23°. The solid dissolved and shortly thereafter crystallisation occured. The stirred mixture was diluted by dropwise addition of diisopropyl ether (20 ml). The solid was collected by filtration to give the *title compound* (3.06 g) as colourless needles. N,N-dimethylformamide by NMR=2½ moles. τ(DMSO-d$_6$): 2.4–3.0 (m, trityl); 3.32 (s, aminothiazole ring proton); 0.47, 1.38, 1.82 (pyridinium protons); 4.34 (m, C-7 proton); 4.92 (d, J-5, C-6 proton); 8.64 (s, t-butyl protons); 8.62 (s, (CH$_3$)$_2$-C<), [α]$_D^{20°}$=−27.5° (α=1.1 in methanol).

(b)

(6R,7R)-7-[(Z)-2-(2-Aminothiazol-4-yl)-2-(Carboxy-prop-2-oxyimino)acetamido]-3-(1-pyridiniummethyl)-ceph-3-em-4-carboxylate dihydrochloride

The product from Stage (a) (2.1 g) was dissolved in formic acid (10 ml) at 22°. Concentrated hydrochloric acid (0.8 ml) was added and after 75 minutes, the precipitated solid was filtered off. The filtrate was evaporated and industrial methylated spirits (10 ml) was added. The solution was re-evaporated. The residue was dissolved in methanol and the solution added to diisopropyl ether, giving the *title compound,* (1.35 g) [α]$_D^{20°}$−14.7° (c, =0.95 in pH 6 buffer) τ(DMSO-d$_6$) 0.28 (d, J 9, —CO—NH), 0.77 (d, J 6), 1.25 (t, J 6), 1.70 (t, J 6, pyridinium ring protons); 3.0 (s, aminothiazole protons); 3.99 (dd, J 9 and 5, 7-H); 4.67 (d, J 5, 6-H); 8.42 (s, —(CH$_3$)$_2$).

EXAMPLE 7

(6R,7R)-7-[(Z)-2-Methoxyimino-2-(2-tritylaminothiazol-4-yl)-acetamido]-3-(1-pyridiniummethyl)ceph-3-em-4-carboxylate A suspension of $PCl_5$ (1.89 g) in dichloromethane (35 ml) was cooled to $-5°$ and (Z)-2-methoxyimino-2-(2-tritylaminothiazol-4-yl)acetic acid (4.03 g) was added. The resulting solution was stirred at 0° to $-5°$ for ½ hour. Triethylamine (2.4 ml) was added followed by distilled water (13 ml). The resulting biphasic solution was stirred at ca 0° for 10 minutes and then the lower phase was added over 2 minutes to a suspension of (6R,7R)-7-amino-3-(1-pyridiniummethyl)ceph-3-em-4-carboxylate dihydrochloride dihydrate (3.15 g) in dichloromethane (18 ml), dimethylformamide (18 ml), and triethylamine (4.4 ml) at 0° to $-5°$. The resulting reaction mixture was stirred at ca 0° for 1½ hours. Methanol (1 ml) was added followed 5 minutes later by distilled water (66 ml). The mixture was stirred for 5 minutes and then stood at ca 4° for 16 hours. The organic phase was separated and the aqueous phase extracted with dichloromethane (30 ml). The resulting emulsion would not separate and organic solvents were removed under reduced pressure. The aqueous solution was decanted off the brown oil and this oil dissolved in dichloromethane (20 ml). The dichloromethane solutions were combined, dried over magnesium sulphate and evaporated under reduced pressure to a gum. Trituration of this gum with acetone (100 ml) and isopropyl ether (100 ml) gave a solid product which was filtered off, washed with isopropyl ether (20 ml), and dried at 40° in vacuo to give the *title compound* (5.34 g) $\tau$ (DMSO-$d_6$) 0.48 (d, J 8 Hz, NH), 0.60 (d, J 6 Hz, pyridinium C-2 and C-6H), 1.21 (s, —NH), 1.54 (t, J 6 Hz, pyridinium C-4H), 1.76 (d, J 6 Hz, pyridinium C-3 and C-5H), 2.68 (s, phenyl H), 3.29 (s, thiazole H), 4.2–4.5 (m, C-7H), 4.1–4.8 (m, C-3 CH$_2$), 4.88 (d, J 5 Hz, C-6H), 6.20 (s, oxime CH$_3$), 6.39–6.83 (ABq, J 18 Hz, C-2 CH$_2$).

EXAMPLE 8

(6R,7R)-7-[(Z)-2-(2-Aminothiazol-4-yl)-2-methoxyiminoacetamido]-3-(1-pyridiniummethyl)ceph-3-em-4-carboxylate, dihydrochloride, dihydrate A solution of (6R,7R)-7-[(Z)-2-methoxyimino-2-(2-tritylaminothiazol-4-yl)acetamido]-3-(1-pyridiniummethyl)ceph-3-em-4-carboxylate (10.3 g) in formic acid (30.9 ml) was stirred at ambient temperature for 15 minutes. Concentrated hydrochloric acid (5.15 ml) was added and the reaction mixture was stirred for a further 5 minutes. The triphenyl carbinol was filtered off and the combined filtrate and washings were evaporated under reduced pressure to ca half volume and acetone (30 ml) was added. The resulting solution was added over 5–10 minutes to a stirred mixture of acetone (180 ml) and isopropyl ether (210 ml) to precipitate the product. The product was isolated by filtration, washed with isopropyl ether (50 ml) and dried at 40° in vacuo to give the *title compound* (6.95 g), $[\alpha]_D -15.5°$ (c 1.034, DMSO), $\lambda_{max}^{H_2O}$ 255 nm (E$_{1\,cm}^{1\%}$ 330), $\tau$(D$_2$O) 1.04 (d, J 6 Hz, pyridinium C-2 and C-6H), 1.37 (t, J 6 Hz, pyridinium C-4H), 1.88 (t, J 6 Hz, pyridinium C-3 and C-5H), 2.88 (s, thiazole H), 4.13 (d, J 5 Hz, C-7H), 4.68 (d, J 5 Hz, C-6H), 4.20 and 4.60 (ABq, J 13 Hz, C-3 CH$_2$), 5.96 (s, oxime CH$_3$), 6.24 and 6.65 (ABq, J 18 Hz, C-2 CH$_2$).

EXAMPLE 9

(6R,7R)-7-[(Z)-2-(2-t-Butoxycarbonylprop-2-oxyimino)-2-(fur-2-yl)acetamido]-3-(1-pyridiniummethyl)ceph-3-em-4-carboxylate Oxalyl chloride (2.25 ml) was added to a stirred solution of 2-(Z)-(t-butoxycarbonylprop-2-oxyimino)-2-(fur-2-yl)acetic acid (7.43 g) in dichloromethane (250 ml) containing triethylamine (3.5 ml) and N,N-dimethylformamide (0.5 ml) at 5°. The mixture was stirred at 5° for 1 hour, and then evaporated under reduced pressure to give a semi solid gum. This gum was suspended in acetone (250 ml) and added to a stirred solution of (6R,7R)-7-amino-3-(1-pyridiniummethyl) ceph-3-em-4-carboxylate dihydrochloride dihydrate (10 g) in distilled water (500 ml) and acetone (250 ml) containing sodium hydrogen carbonate (10.0 g), at 5°, over 15 minutes. After the addition, the solution was stirred at 5° for 1.5 hours. The solution was then evaporated under reduced pressure to a volume of ca 200 ml, giving a suspension of a pale yellow solid. The mixture was then acidified from pH 8.2 to 2.0. The solid was collected by filtration and dried in vacuo at 40° to give the *title compound* 9.8 g. $\tau$ (DMSO-$d^6$) 0.49 (pyridyl 2-H+acetamido H, d, J 8 Hz), 1.39 (pyridyl 4-H m), 1.81 (pyridyl 3-H m), 2.2 (furyl 5-H s), 3.2–3.4 (furyl 3-H and 4-H s), 4.26 (C$_{(7)}$-H m), 4.28+4.78 (pyridyl 4-H J=12 Hz m), 4.85 (C$_{(6)}$-H), 6.39+6.89 (C$_{(2)}$-H ab quartet 6.6 J=18 Hz), 8.6 (propyl -H and t-butyl -H d).

EXAMPLE 10

(6R,7R)-7-[(Z)-2-(2-Carboxyprop-2-oxyimino)-2-(fur-2-yl)acetamido]-3-(1-pyridiniummethyl)ceph-3-em-4-carboxylate, hydrochloride, hydrate (6R,7R)-7-[(Z)-2-(2-t-butoxycarbonylprop-2-oxyimino)-2-(fur-2-yl)acetamido]-3-(1-pyridiummethyl)ceph-3-em-4-carboxylate (6.0 g) was dissolved in formic acid (45 ml), the solution was cooled to 5° and concentrated hydrochloric acid (1.44 ml) was added. The solution was stirred for 1.5 hours at 5°, and then evaporated under reduced pressure to a volume of 10 ml. Acetone (50 ml) was added to the residue and the resultant solution added slowly with stirring to isopropyl ether (250 ml). The cream coloured precipitate was collected by filtration, washed with isopropyl ether (50 ml) and dried in vacuo at 40° to give the *title compound*, 5.65 g, $[\alpha]_D^{20}$ (c, 1.016 H$_2$O) $-24.5°$. $\tau$(D$_2$O) 1.2 (pyridyl 2-H s), 1.49 (pyridyl 4-H m), 1.99 (pyridyl 3-H m), 2.41 (furyl 5-H s), 3.21 (furyl 3-H d), 3.42 (furyl 4-H d), 4.12 (C$_{(7)}$-H d), 4.71 (C$_{(6)}$-H), 4.28+4.69 (C$_{(3)}$-H J=14 Hz m), 6.29+6.71 (C$_{(2)}$-H ab quartet 6.5 J=18 Hz), 8.42 (propyl-H).

EXAMPLE 11

(a)
(6R,7R)-7-Amino-3-(1-pyridiniummethyl)ceph-3-em-4-carboxylate,monoperchlorate Cephaloridine (8.0 g) was dissolved in water (180 ml) at 30°, and the solution adjusted to pH 7.0 with dilute ammonium hydroxide. Sufficient immobilized *E. coli* amidohydrolase enzyme was added, to give an initial rate of hydrolysis of 0.5 mmol min$^{-1}$ and the suspension stirred for 1.5 hours, maintaining the pH at 7.0 by titration with dilute ammonium hydroxide. The enzyme was filtered from the aqueous reaction mixture, and following the above procedure used twice more with fresh starting material (2×8 g). The combined aqueous filtrates were stirred with charcoal and filtered through a bed of 'diatomaceous earth'. The clarified filtrate was diluted with isopropyl alcohol (2.4 liters), treated with 60% aqueous perchloric acid (38.5 g) and cooled to 0° C. The suspension was filtered and the solid washed successively with 20% aqueous isopropyl alcohol, isopropyl alcohol and isopropyl ether and dried to give the *crystalline title compound* (20.6 g). $[\alpha]_D^{22}$ (c, 1.0 pH 6.0, 2 M phosphate) −54°, $\lambda_{max}$ (pH 6 buffer) 259 ($E_{1\ cm}^{1\%}$ 326, $\epsilon$12,800) and $\lambda_{infl}$ at 264 ($E_{1\ cm}^{1\%}$ 301, $\epsilon$11,800) and 274 ($E_{1\ cm}^{1\%}$ 196, $\epsilon$7,700, impurities by HPLC 1.6%.

(b) Cephaloridine hydronitrate (9.2 g) was treated with enzyme and the product isolated as described in Example 11(a) to give the *crystalline title compound* (20.0 g). $[\alpha]_D^{22}$ (c, 1.0 pH 6, 0.2 M phosphate) −53°, $\lambda_{max}$ 258.5 ($E_{1\ cm}^{1\%}$ 324, $\epsilon$12,700) and $\lambda_{infl}$ 264 ($E_{1\ cm}^{1\%}$ 298, $\epsilon$11,700) and 274 ($E_{1\ cm}^{1\%}$ 194, $\epsilon$7,600). Impurities by HPLC 1.6%.

EXAMPLE 12

(a)

(6R,7R)-7-Amino-3-(1-pyridiniummethyl)ceph-3-em-4-carboxylate,dihydrochloride dihydrate The product from Example 11(a) (20.0 g) was dissolved in a mixture of distilled water (50 ml), Amberlite LA-2 liquid ion exchange resin and ethyl acetate (25 ml), and the two phase solution stirred for 10 minutes at room temperature. The lower aqueous layer was separated and stirred with Amberlite LA-2 (12.5 ml) and ethyl acetate (12.5 ml) for 10 minutes. The aqueous layer was separated, washed with ethyl acetate (10 ml), cooled to 5° C., and treated with concentrated hydrochloric acid (15.0 ml) and isopropyl alcohol (360 ml). The suspension was filtered and the solid washed with isopropyl alcohol and dried to give the *crystalline title compound* (18.7 g). $[\alpha]_D^{22}$ (c, 1.0 pH 6, 0.4 M phosphate) −51°, $\lambda_{max}$ 259 ($E_{1\ cm}^{1\%}$ 323, $\epsilon$12,900) and $\lambda_{infl}$ 264 ($E_{1\ cm}^{1\%}$ 299, $\epsilon$12,000) and 274 ($E_{1\ cm}^{1\%}$ 194, $\epsilon$7,800). Impurities by HPLC 0.7%.

(b) The product from Example 11(b) (19.2 g), was converted by the procedure as described above in Example 12(a) to give the *crystalline title compound* (18.1 g). $[\alpha]_D^{22}$ (c, 1.0 pH 6, 0.4 M phosphate) −52°, $\lambda_{max}$ 259 ($E_{1\ cm}^{1\%}$ 322, $\epsilon$12,900) and $\lambda_{infl}$ 264 ($E_{1\ cm}^{1\%}$ 299, $\epsilon$12,000) and 274 ($E_{1\ cm}^{1\%}$ 196, $\epsilon$7,800). Impurities by HPLC 1.7%.

We claim:

1. The N,N-dimethylformamide solvate of (6R,7R)-7-[(Z)-2-(2-tritylaminothiazol-4-yl)-2-(2-t-butoxycarbonylprop-2-oxyimino)acetamido]-3-(1-pyridiniummethyl)ceph-3-em-4-carboxylate.

* * * * *